United States Patent
Suuronen

(10) Patent No.: US 6,614,875 B2
(45) Date of Patent: Sep. 2, 2003

(54) METHOD AND APPARATUS FOR IMAGING THE HEAD AREA OF A PATIENT

(75) Inventor: Esa Suuronen, Kerava (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/967,156

(22) Filed: Sep. 28, 2001

(65) Prior Publication Data
US 2002/0041652 A1 Apr. 11, 2002

(30) Foreign Application Priority Data
Oct. 11, 2000 (FI) .............................. 20002239

(51) Int. Cl.[7] ................................ G01N 23/04
(52) U.S. Cl. ............................ 378/63; 378/205
(58) Field of Search .................... 378/63, 205, 206, 378/170, 62, 38, 39, 40

(56) References Cited

U.S. PATENT DOCUMENTS

| 5,177,775 A | 1/1993 | Onodera et al. |
| 5,511,106 A | 4/1996 | Doebert et al. |
| 5,539,798 A * | 7/1996 | Asahina et al. ............ 378/98.5 |
| 6,229,873 B1 * | 5/2001 | Bani-Hashemi et al. ...... 378/63 |
| 6,305,842 B1 * | 10/2001 | Kunert ........................ 378/206 |
| 6,379,041 B1 * | 4/2002 | Schuetz et al. ............. 378/205 |
| 6,435,717 B1 * | 8/2002 | Kohler et al. ............... 378/206 |

FOREIGN PATENT DOCUMENTS

EP  1 089 067  4/2001

* cited by examiner

Primary Examiner—Drew A. Dunn
Assistant Examiner—Irakli Kiknadze
(74) Attorney, Agent, or Firm—Andrus, Sceales, Starke & Sawall, LLP

(57) ABSTRACT

The invention relates to a method and apparatus for imaging the head area of a patient by taking both cephalometric X-ray and photographic images of desired objects to be imaged. The method is conducted by using a mechanism (1) applicable to cephalometric X-ray imaging, which comprises an X-ray source (5) in front of an object, an X-ray receiving element behind the object, and patient positioning implements (8–10). The apparatus is further fitted with photographic instruments (13) for taking photographs from an object to be imaged. In the method, a patient is placed by means of the patient positioning implements (8–10) in a desired imaging position and imaged in the same imaging position in both modes of imaging.

17 Claims, 2 Drawing Sheets

METHOD AND APPARATUS FOR IMAGING THE HEAD AREA OF A PATIENT

CROSS REFERENCE TO RELATED APPLICATION

The present application claims priority from Finnish Patent Application No. 20002239, filed Oct. 10, 2000.

SUMMARY OF THE INVENTION

The present invention relates to a method for imaging the head area of a patient by taking both cephalometric X-ray and photographic images of desired objects to be imaged, said images being converted to digital mode, if necessary, and conveyed in digital mode to a computer. The invention relates also to an apparatus for imaging the head area of a patient for producing both cephalometric X-ray and photographic images from desired objects to be imaged, and for conveying the images to a computer.

Assistance can be provided for planning dental surgery procedures by using both X-rays depicting the head of a patient (cephalometric X-ray images) and conventional photographs. In this context, the term photograph is used in reference to both film-recorded photographs and images obtained by means of a digital imaging apparatus. If necessary, the obtained cephalometric X-ray images and photographs are first converted to digital mode and then delivered in digital mode to a computer microprocessor, and further to a computer screen for reviewing. With the aid of a computer, the images can be processed as desired, for example by superimposing (morphing) the same to obtain a more perceptive image for assisting in the performance of surgical procedures, and also to obtain an outlook regarding the impact of a surgical operation on the appearance of a patient. The computer can be e.g. a personal computer (PC), or a computer integrated in the imaging apparatus. In the prior art, these cephalometric X-ray images and photographs have been taken with separate instruments, whereby a patient must be specifically positioned or aligned for each mode of imaging, which is time consuming and causes problems, e.g. in terms of providing an imaging geometry as uniform as possible for each mode of imaging. In addition, the use of two separate mechanisms requires a considerable amount of space. Hence, it is an object of the present invention to provide an improvement over the available methods and equipment, said improvement enabling a faster-than-before imaging process in two different modes of imaging and, in addition, the preservation of an imaging geometry will be essentially simpler than before. One further benefit is also that considerably less space will be required.

BRIEF DESCRIPTION OF THE INVENTION

In order to accomplish such objects of the invention, a method of the invention is characterized in that the method involves the use of a mechanism applicable to cephalometric X-ray imaging, comprising an X-ray source in front of an object to be imaged, an X-radiation receiving element behind the object, and patient positioning implements, in which method a patient is placed by means of the patient positioning implements in a desired imaging position and imaged in the same imaging position in both modes of imaging. Regarding its preferred embodiments, the inventive method is set forth in the claims.

On the other hand, an apparatus of the invention is characterized in that the apparatus comprises a mechanism applicable to cephalometric X-ray imaging, which is provided with an X-ray source in front of an object to be imaged, an X-radiation receiving element behind the object, and patient positioning implements, and that the apparatus is further fitted or, if necessary, can be fitted with photographic instruments for taking photographs of an object to be imaged, the patient being positionable by means of the patient positioning implements in a desired imaging position and capable of being imaged in the same imaging position in both modes of imaging.

BRIEF DESCRIPTION OF THE DRAWING

The invention will now be described in more detail with reference to the accompanying drawings, in which.

DETAILED DESCRIPTION OF THE INVENTION

Figure 1:
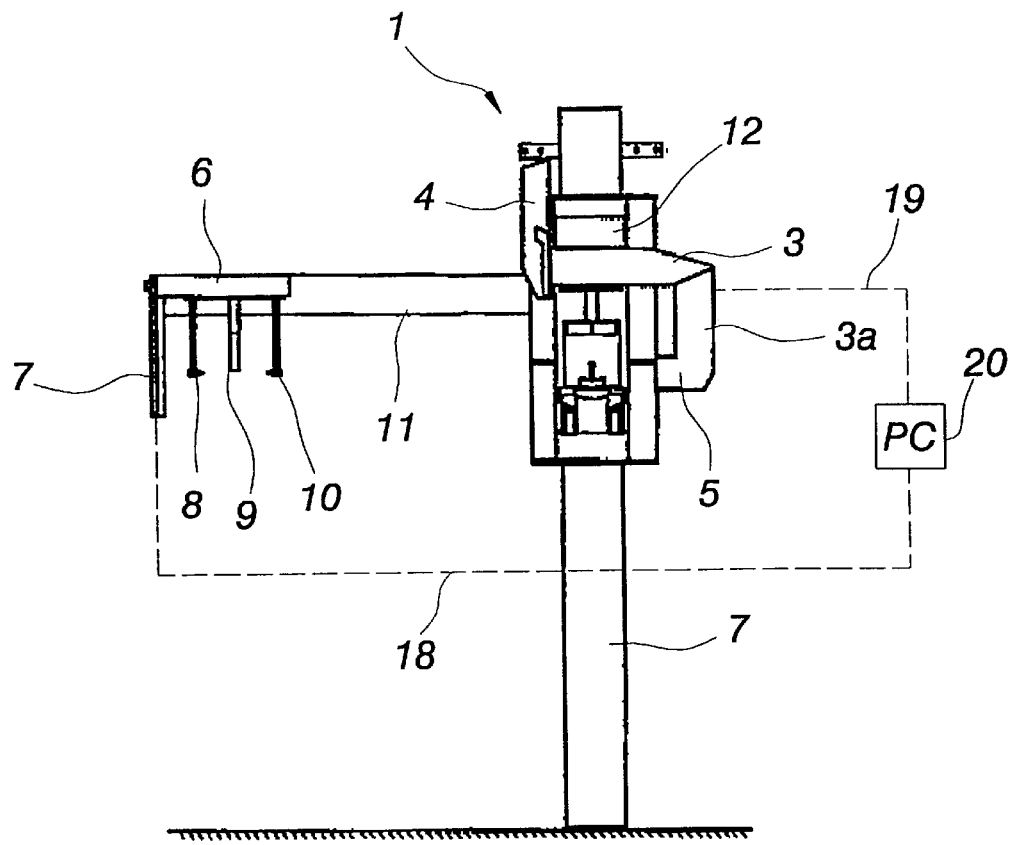
FIG. 1 shows in a schematic elevation one embodiment of a mechanism applicable for use in the invention.
Figure 2:
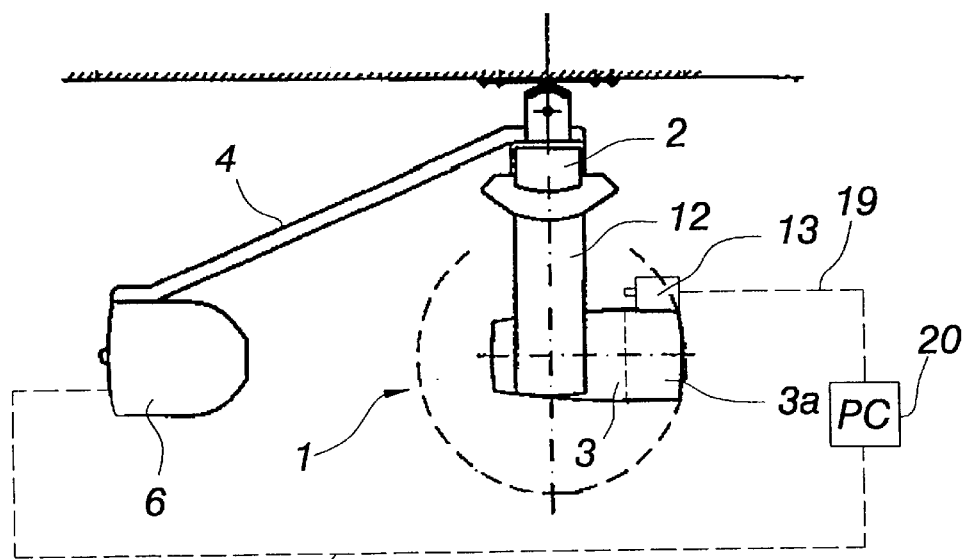
FIG. 2 shows the mechanism of FIG. 1 in a plan view.

FIGS. 1 and 2 depict schematically a panoramic X-ray apparatus provided with instruments needed for cephalometric X-ray imaging, which comprises a horizontal arm 12, mounted on an upright 2 and having its end provided with a C-arm 3 capable of pivoting relative to the horizontal arm 12. The C-arm 3 includes a vertically movable leg 4, which is provided with X-radiation receiving elements intended for panoramic imaging, e.g. an X-ray film or a digital detector. The C-arm has its second leg 3a fitted with an X-ray source 5. For cephalometric X-ray imaging, the apparatus is fitted with a boom element 11, the end of which carries a cephalometric X-ray imaging device 6, including a vertical member 7 which is to be positioned behind the head of a patient and which carries an X-radiation receiving element, e.g. an X-ray film or a digital detector, e.g. a CCD detector. In the illustrated embodiment, a digital detector is connected over a communication link represented by a dashed line 18 to a computer (PC) 20. The communication link can be wired or wireless (e.g. a radio link or IR connection). The cephalometric X-ray imaging device 6 is further provided with braces 8, 9 and 10 needed for patient positioning. This type of apparatus applicable to cephalometric X-ray imaging is as such well known to a person skilled in the art, and shall not be described further in this context. The inventive apparatus comprises additionally a photographic camera 13 mounted e.g. on the leg 3a of the C-arm 3 carrying the X-ray source 5, which can be a camera recording on standard photographic film or e.g. a video camera capable of taking so-called still pictures. The camera 13 is mounted on the leg 3a, such that the camera 13 and the X-ray source 5 can be positionally reversed by comparatively simple procedures in such a way that each camera will be capable of taking images from the head area of a patient with an essentially identical imaging geography. The leg 3a carrying the X-ray source 5 and the camera 13 can be e.g. articulated relative to the frame element of the C-arm 3 to be pivotal in a direction lateral to the imaging direction and clampable in a variety of positions, such that the camera 13 and the X-ray source 5 can be reversed by a simple and quickly effected pivotal action.

In the illustrated embodiment, the camera 13 is connected over a communication link 19 to the computer 20.

In FIGS. 1 and 2, the photographic camera 13 is depicted as integrated in a cephalometric X-ray imaging apparatus, but it can also be a separate photographic camera, having clamp elements therefor provided in conjunction with a cephalometric X-ray imaging apparatus for aligning the photographic camera in such a way that photography can be performed with imaging geometries essentially the same as those used for cephalometric X-ray imaging.

Figure 4:
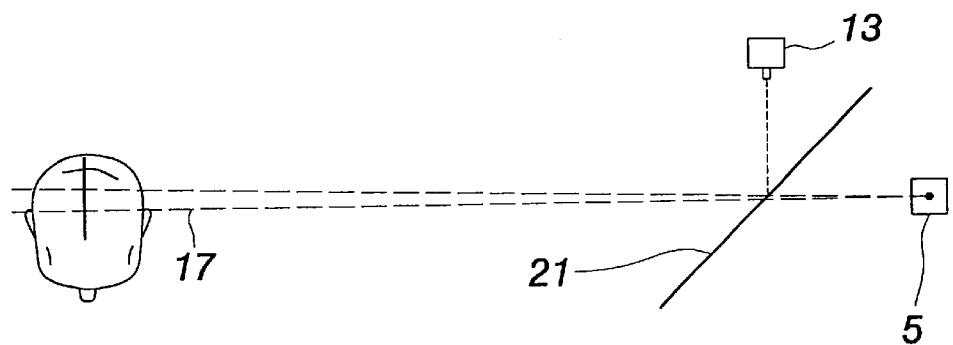
FIG. 4 shows in a diagrammatic view an alternative disposition of a photographic camera used in the invention.

Instead of the embodiment shown in FIGS. 1 and 2, wherein locations of the photographic camera 13 and the X-ray source 5 are reversed, the photographic camera 13 can be installed in a cephalometric X-ray imaging apparatus also as shown in FIG. 4, such that the photograph will be taken by way of a mirror 21, said mirror being designed to be penetrable to X-rays 17 and said mirror being aligned relative to the field of X-rays in view of taking a photograph with imaging geometries essentially identical to those used for cephalometric X-ray imaging.

Figure 3:
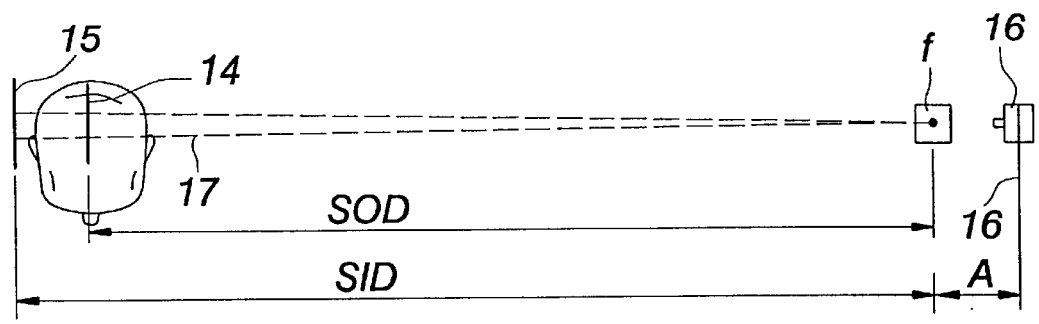
FIG. 3 shows in a diagrammatic view a relative disposition of imaging instruments used in the invention.

FIG. 3 illustrates further in a preferred implementation a relative disposition regarding a focus f for the X-ray source 5 and an imaging plane 16 for the camera 13, the latter carrying a film or a digital sensor. Reference numeral 17 represents a cone of rays or a beam emitted from the X-ray source, which in cephalometric X-ray imaging advances through an imaging plane 14 to a detector-equipped image plane 15. The imaging plane 14 lies typically at the depthwise centre of a patient's skull. Thus, the ratio of magnification in imaging is equal to the ratio of distance (SID) between the focus f and the image plane 15 to a distance (SOD) between the focus f and the imaged layer 14. The camera 13 has its film plane 16 preferably placed at a distance A, which corresponds to the distance (SID)-(SOD), from the site of the focus f, whereby the imaging geometry will be essentially consistent with the geometry of cephalometric X-ray imaging.

The patient positioning implements 6–10 are preferably provided with reference implements (not shown), which are imaged both in cephalometric X-ray images and photographs, the image information obtained from the reference implements being useful in specifying the dimensions of cephalometric X-ray images and photographs, as well as assisting in the superimposing of images obtained from various modes of imaging. The reference implements may include for example a measuring scale.

One way of using the inventive method and apparatus is to take images first in one mode of imaging, and then in the other, for example cephalometric X-ray imaging first and then photography, or vice versa. It is also conceivable to perform both modes of imaging concurrently, e.g. by means of a mirror arrangement shown in FIG. 4.

What is claimed is:

1. An apparatus for imaging a head area of a patient to obtain a cephalometric X-ray image and a corresponding photographic image of a desired object in the head area, said apparatus comprising:
    an upright support (2);
    an arm arrangement (3,12) coupled to the upright support;
    an X-ray source (5) coupled to said arm arrangement;
    a cephalometric X-ray imaging device (6) mounted to said upright support and having a member (7) for positioning an X-radiation receiving element behind the object desired to be imaged so that said X-radiation receiving element obtains a cephalometric X-ray image;
    a positioning implement (8,9,10) for positioning the object desired to be imaged with respect to said X-radiation receiving element; and
    a camera (13) for taking a photographic image of the object to be imaged, said camera being coupled to said apparatus such that said camera and the X-ray source use substantially the same imaging geometry when obtaining both said cephalometric X-ray image and said photographic image, said X-ray source and said camera being interchangeably positioned in the apparatus for obtaining images of the object with substantially the same imaging geometry.

2. The apparatus of claim 1, wherein said camera is coupled to said apparatus such that said camera and said X-ray source are in a fixed relationship to each other.

3. The apparatus of claim 1, wherein said X-ray source and said camera are pivotally mounted on said arm arrangement for carrying out the interchangeable positioning of said X-ray source and said camera.

4. The apparatus of claim 1, further comprising a mirror (21), said mirror being penetrable to X-rays, and wherein said camera is coupled to said apparatus and said mirror is aligned relative to a field of X-rays so as allow for taking of said photograph image and said cephalometric X-ray image with substantially the same imaging geometry.

5. The apparatus of claim 1, wherein said positioning implement has a reference element for specifying a dimension of said cephalometric X-ray image and said photographic image.

6. The apparatus of claim 1, wherein said camera comprises a digital camera.

7. The apparatus of claim 1, wherein said camera is detachably coupled to said apparatus.

8. A method for taking both a cephalometric X-ray image and a photographic image of an object desired to be imaged in the head area of a patient using essentially the same imaging geometry, said method comprising the steps of:
    providing an apparatus having an upright support (2); an arm arrangement (3,12) coupled to the upright support, an X-ray source (5) coupled to the arm arrangement; a cephalometric X-ray imaging device (6) mounted to the upright support and having a member (7) for positioning an X-radiation receiving element behind the object desired to be imaged so that the X-radiation receiving element obtains a cephalometric X-ray image; and a positioning implement (8,9,10) for positioning an object desired to be imaged with respect to the X-radiation receiving element; providing a camera (13), said camera being capable of obtaining a photographic image and being coupled to said apparatus such that the camera and the X-ray source use essentially the same imaging geography when obtaining a cephalometric X-ray image and a photographic image;

positioning the object desired to be imaged with respect to the X-radiation receiving element;

obtaining an image with one of the X-radiation receiving element and the camera;

interchanging the position of the camera and the X-ray source such that a photographic image and an X-ray image of the object will be obtained using substantially the same imaging geometry; and obtaining an image with the other of the camera and X-radiation receiving element.

9. The method of claim 8, further defined as obtaining a digital photographic image.

10. The method of claim 8, wherein said cephalometric X-ray image and said photographic image are formed in a digital mode for transfer over wire communication.

11. The method of claim 8, wherein said cephalometric X-ray image and said photographic image are formed in a digital mode for transfer over wireless communication.

12. The method of claim 8, wherein the cephalometric X-ray image and the photographic image are formed in a digital mode and transferred over a wire communication to a computer.

13. The method of claim 8, wherein said cephalometric X-ray image and said photographic image are formed in a digital mode and transferred over a wireless communication to a computer.

14. The method of claim 8, wherein said object desired to be imaged is positioned using the positioning implement.

15. The method of claim 14, further comprising the step of using a reference element in the positioning implement for determining dimension in the cephalometric X-ray image.

16. The method of claim 14, further comprising the step of using a reference element in the positioning implement for determining dimensions in the photographic image.

17. The method of claim 14, further comprising the step of using a reference element in the positioning implement for the superimposing a photographic image and a cephalometric X-ray image.

* * * * *